United States Patent [19]

Matouk et al.

[11] Patent Number: 5,625,684

[45] Date of Patent: Apr. 29, 1997

[54] ACTIVE NOISE SUPPRESSION SYSTEM FOR TELEPHONE HANDSETS AND METHOD

[75] Inventors: Anthony F. Matouk, Los Altos; Dieter Enzmann, Menlo Park; Ahmet Karakasoglu, Palo Alto, all of Calif.

[73] Assignee: Local Silence, Inc., Palo Alto, Calif.

[21] Appl. No.: 206,462

[22] Filed: Mar. 4, 1994

Related U.S. Application Data

[63] Continuation-in-part of Ser. No. 38,336, Feb. 4, 1993, abandoned.

[51] Int. Cl.[6] ................................................. H04M 1/00
[52] U.S. Cl. ........................... 379/387; 379/390; 379/419; 379/433; 381/71
[58] Field of Search ...................................... 379/387–392, 379/406, 410, 419, 432, 433; 381/71, 92, 93, 94, 95

[56] References Cited

U.S. PATENT DOCUMENTS

| | | | |
|---|---|---|---|
| 4,672,674 | 6/1987 | Clough et al. | 381/71 |
| 4,908,855 | 3/1990 | Ohga et al. | 379/387 |
| 4,912,767 | 3/1990 | Chang | 381/47 |
| 5,121,426 | 6/1992 | Baumhauer, Jr. et al. | 379/388 |
| 5,131,047 | 7/1992 | Hashimoto et al. | 381/71 |
| 5,148,471 | 9/1992 | Metroka et al. | 379/58 |
| 5,201,006 | 4/1993 | Weinrich | 381/93 X |
| 5,239,578 | 8/1993 | Regen et al. | 379/387 |
| 5,251,263 | 10/1993 | Andrea et al. | 381/71 |
| 5,319,736 | 6/1994 | Hunt | 395/2.36 |
| 5,323,458 | 6/1994 | Park et al. | 379/410 X |
| 5,335,276 | 8/1994 | Thompson et al. | 380/21 |
| 5,343,521 | 8/1994 | Jullien et al. | 379/410 |
| 5,381,473 | 1/1995 | Andrea et al. | 379/387 |
| 5,406,622 | 4/1995 | Silverberg et al. | 379/307 |
| 5,444,786 | 8/1995 | Raviv | 381/71 |
| 5,452,361 | 9/1995 | Jones | 381/71 |
| 5,471,538 | 11/1995 | Sasaki et al. | 381/94 X |
| 5,473,702 | 12/1995 | Yoshida et al. | 381/94 |
| 5,481,615 | 1/1996 | Eatwell et al. | 381/71 |
| 5,493,616 | 2/1996 | Iidaka et al. | 381/71 |
| 5,526,421 | 6/1996 | Berger et al. | 379/389 |

FOREIGN PATENT DOCUMENTS

| | | | |
|---|---|---|---|
| 3004784 | 8/1991 | Germany | 379/388 |
| 1-042966 | 2/1989 | Japan | 379/419 |
| 1202960 | 8/1989 | Japan | 379/395 |
| 2-250556 | 10/1990 | Japan | 379/433 |
| 9217019 | 10/1992 | WIPO | 379/433 |

OTHER PUBLICATIONS

Abstract: Full-duplex speakerphone with acoustic and electric echo-canceller utilizing the DSP56200 cascadable adaptive FIR filter chip, *Proc. of Midcon/90 Technical Conference on Electronic and Electrical Technology*, Dallas Tx, Sep. 11–13, 1990.

*Primary Examiner*—Krista M. Zele
*Assistant Examiner*—Scott L. Weaver
*Attorney, Agent, or Firm*—Flehr, Hohbach, Test, Albritton & Herbert

[57] ABSTRACT

System for use by a caller and a recipient of a telephone call for suppressing environmental noise in the vicinity of a telephone comprising a telephone handset forming a part of the telephone. The telephone handset has a human voice sensor for picking up human sounds generally in one direction, and creating a first electrical signal. A speaker capable of producing substantially directional human voice sounds is provided. A second sound sensor is carried by the handset and has sound pick-up capabilities from a direction which is generally opposite said one direction for picking up external environmental noise in the vicinity of the handset and producing a second electrical signal having a frequency and amplitude. Electrical circuitry is provided for processing the second electrical signal to provide a third electrical signal of the same frequency as the second electrical signal but of opposite amplitude and sign and for combining the third electrical signal with the first electrical signal to suppress environmental noise present in the first electrical signal so that the recipient will receive an electrical signal in which the environmental noise in the vicinity of the caller has been suppressed.

6 Claims, 2 Drawing Sheets

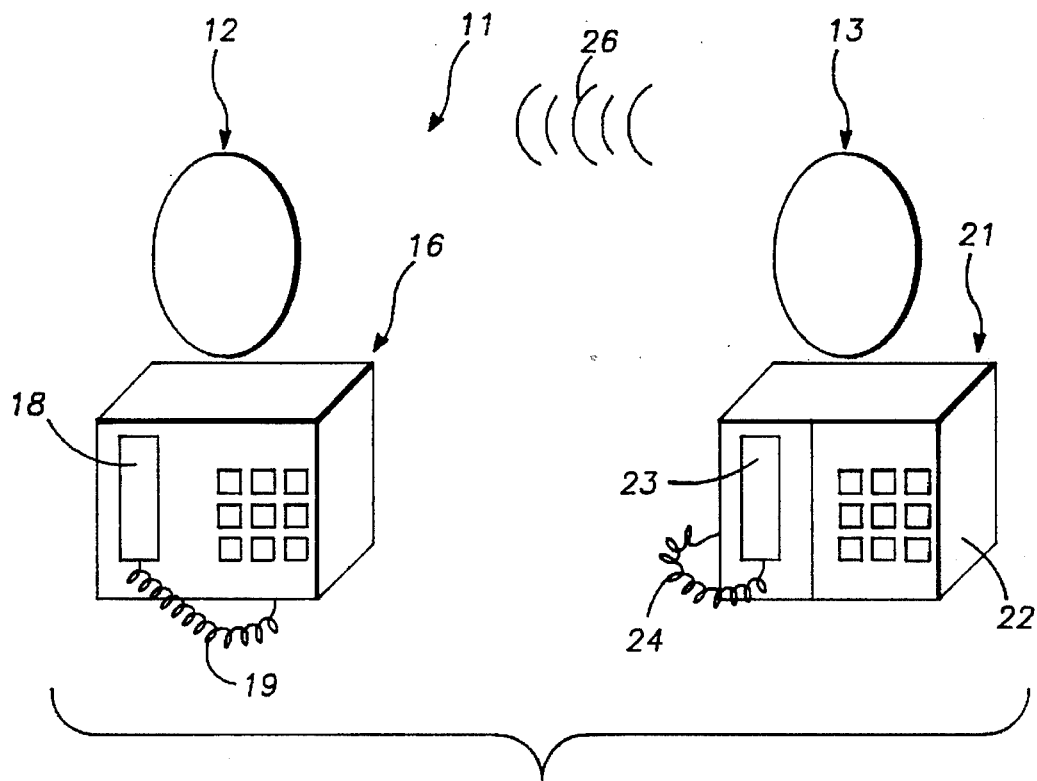
FIG.—1
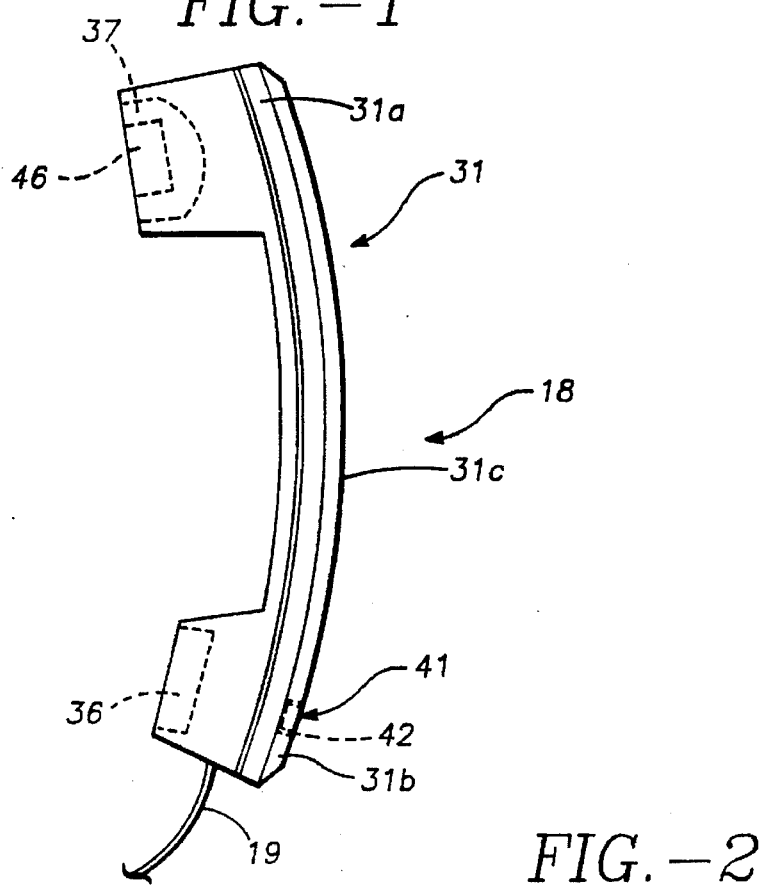
FIG.—2

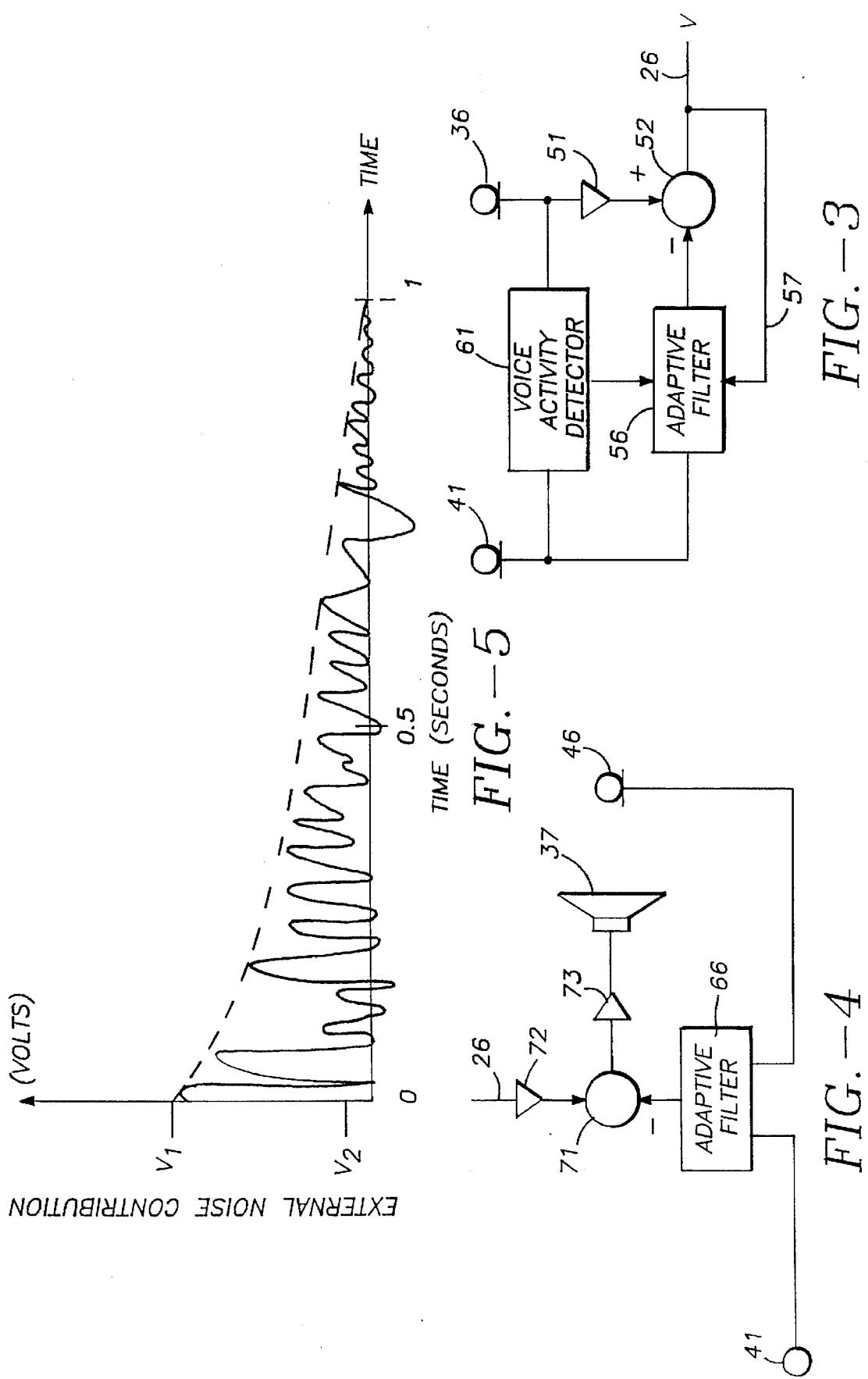

5,625,684

ACTIVE NOISE SUPPRESSION SYSTEM FOR TELEPHONE HANDSETS AND METHOD

This is a continuation-in-part of application Ser. No. 08/038,336 filed Feb. 4, 1993, abandoned.

This invention relates to an active noise suppression system for telephone handsets and method for suppressing environmental noise.

There has been continued difficulty in utilizing telephone handsets in noisy environments because of background noise. For example, in making telephone calls in airplanes, it has been difficult for the user on the airplane and also the recipient to carry on normal conversations because of the background noise, as for example the noise from the jet engines utilized to propel the aircraft. Similarly, for cellular telephone users in automobiles, the noise from freeway traffic has also been troubling. There are many other situations where the ambient noise makes it difficult to use telephone handsets. This can include construction sites, airport sites, street sites and the like. The use of telephone booths for shielding has proved to be inadequate in many situations to overcome this problem.

In general, it is an object of the present invention to provide an active noise suppression system and method for telephone handsets.

Another object of the invention is to provide such a system and method which is particularly suitable for noisy environments.

Another object of the invention is to provide a system and method of the above character in which environmental noise is suppressed so that it does not have an appreciable affect on telephone conversations.

Additional objects and features of the invention will appear from the following description in which the preferred embodiments are set forth in conjunction with the accompanying drawings.

FIG. 1 is a schematic illustration of a telephone system incorporating the present invention showing the caller in a noisy environment and a recipient in a conventional office or home environment.

FIG. 2 is an enlarged partially schematic view of a telephone handset incorporating the present invention.

FIG. 3 is a block diagram of the circuitry incorporating the present invention which is utilized for suppressing actual environmental noise to the recipient of the call from a person placing the call in a noisy environment.

FIG. 4 is a block diagram of the circuitry incorporating the present invention utilized for suppressing actual environmental noise for the caller utilizing a telephone in a noisy environment.

FIG. 5 is a graph showing the noise suppression which can be achieved utilizing the present invention.

In general, the system of the present invention is for use by a caller and a recipient for suppressing environmental noises in the vicinity of a telephone handset of the caller having a directional voice sensor for picking up human sounds, generally in one direction, and creating a first electrical signal. The handset also has a speaker capable of producing directional human voice sounds. A second sound sensor is carried by the handset for picking up external environmental noise in the vicinity of the handset and faces in a direction which is generally opposite said one direction and produces a second electrical signal having a frequency and amplitude. Means is provided for processing the second electrical signal to provide a third electrical signal of the same frequency as the second electrical signal but of opposite amplitude and sign. Means is provided for combining the third electrical signal with the first electrical signal to suppress any environmental noise present in the first electrical signal so that the recipient will receive a combined electrical signal which is substantially free of the environmental noise in the vicinity of the caller.

More specifically, as shown in FIG. 1 of the drawings, there is provided a telephone system 11 in a caller location 12 in a noisy environment of a type hereinbefore described, as for example in an airplane, automobile and other locations and a recipient location 13 in a conventional home or office environment. The caller location 12 is provided with a telephone station 16 of a suitable type, as for example a car phone which typically includes a console 17 and a handset 18 connected to the console 18 by a cord 19. Similarly, the recipient is provided with a telephone station 21 which consists of a console 22 of a conventional type that is provided with a handset 23 connected by a cord 24 to the console 22. The two stations 16 and 21 can be interconnected in a conventional manner such as by the use of a hard wire, radio frequency, microwave frequencies and fiber optics which are indicated by a microwave link 26.

The handset 18 of the telephone station 16 which is located in the noisy environment is shown in more detail in FIG. 2 and consists of a housing 31 which is provided with two enlarged end portions 31a and 31b facing generally in the same direction with an intermediate portion 31c which is adapted to be grasped by the human hand to hold the portion 31a to the users ear while the other portion 31b can be held in close proximity to the mouth of the user. The end portion 31b carries a first sound sensor 36 in the form of a conventional electromechanical device such as a microphone which is utilized for converting voice signals to an electrical signal having a frequency and amplitude. As shown, the first voice sensor 36 is positioned so that it is substantially directional, i.e. preferably receiving a sound in a direction which is perpendicular to the face of the first sound sensor 36.

The handset 18 also includes a speaker 37 which is provided in the portion 31a. It is also an electromechanical device which converts electrical signals to sound signals. As shown in FIG. 2, the speaker 37 faces generally in a direction which is perpendicular to the axis of the intermediate portion 31c whereas the portion 31a faces in a direction which is inclined slightly from the intermediate portion 31c so that it is adapted to be placed in front of the mouth of the user. The portions of the handset 18 thus far described are conventional.

In accordance with the present invention, a second sound sensor 41 is provided in the handset 18 in the vicinity of the first voice sensor 36 but facing generally in an opposite direction than that of the first sound sensor 36. The second sound sensor 41 is also an electromechanical device and can be in the form of a microphone for converting sound signals to an electrical signal.

Also in accordance with the present invention, a third sound sensor 46 can be provided on the handset 18 and is located in the portion 31a and faces in the same direction as the speaker 37. Thus, as shown in FIG. 2, it can be centrally disposed within the confines of the speaker 37 so that it is in close proximity to the speaker 37 and is oriented so that it faces in a direction very similar to the speaker 37 for picking up any environmental noise which may be present in the region immediately surrounding the space forward of the speaker 37.

Operation of the first and second sound sensors 41 and 46 in connection with the present invention in utilizing the handset 18 in a noisy location may now be briefly described as follows in conjunction with the block diagrams as shown in FIGS. 3 and 4. Let it be assumed that the caller is in an automobile and has a car telephone and wishes to make a call during very noisy conditions, as for example passing truck traffic on a busy freeway or alternatively on an airplane wishing to make a call on the telephone on the plane. The caller at location 12 picks up the handset 18 and utilizes the same in a conventional manner to place a call to the recipient at the recipient location 13. As soon as the circuit is established between the caller 12 and the recipient 13, the circuitry which is shown in FIG. 3 is operable. Assuming that the caller is speaking, the caller's voice is picked up by the microphone 36 which converts the voice signal into an electrical signal having a frequency and amplitude corresponding to the voice signal. The electrical signal created is supplied through an amplifier 51 to a summer 52. At the same time that the caller's voice is being picked up by the first sound sensor 36 in the form of a microphone, the externally generated actual environmental noise surrounding the handset 18 is also being picked up by the second sound sensor or microphone 41. Since this sound sensor 41 is directed in a generally opposite direction of the microphone 36 it will not pick up any substantial sounds from the voice of the caller but will principally pick up the actual environmental sounds which are surrounding the handset 18. This actual environmental noise is converted to a second electrical signal having a frequency and amplitude or phase corresponding to the actual environmental noise and is supplied to an adaptive filter 56 of the type described in co-pending application, Ser. No. 08/206,464, filed Mar. 4, 1994, which converts the second electrical signal into a third electrical signal of the same frequency but of opposite amplitude and sign or 180° out of phase of with the second electrical signal. The third electrical signal is supplied to the summer 52 to in effect suppress the environmental noise which may have been picked up by the first sound sensor 36 to provide a combined output which is supplied to the link 26 connecting the caller to the recipient so that the recipient receives an electrical signal which carries the caller's voice but in which the ambient environmental noise present at the handset 18 of the caller is largely suppressed or minimized so that the recipient can hear the caller's voice with clarity. If the environmental noise has not been suppressed to a desired level, the error in the suppression is picked up and supplied by the feedback loop 57 to the filter 56 so that an appropriate correction can be made by the adaptive filter 56 to supply a corrected third electrical signal to the summer 52. This procedure continues until sufficient correction has been made to bring the combined signal provided on the link 26 is such so that the level of environmental noise present in the signal received by the recipient is below a desired threshold level.

In order to prevent the adaptive algorithm which is utilized by the adaptive filter 56 from being operative both during the time a voice signal is being received from the first sound sensor 36 and external environmental noise is being received from the second sound sensor 41, a voice activity detector 61 is connected to the first and second sound sensors 36 and 41 and to the adaptive filter 56. The voice activity detector 61 can be of a type well known to those skilled in the art. It can be implemented in the same chip used for the adaptive filter 56 by incorporating computational algorithms that monitor the performance by making use of exponential or sliding window-based estimators. With the voice activity detector 61 in use, the adaptive filter 56 is continually operative utilizing the signal received from the external noise sound sensor 41 and supplies a signal utilizing the adaptive algorithm to provide the third electrical signal of the same frequency but of opposite amplitude and sign or 180° out of phase to the summer 52. As soon as the caller speaks this is picked up by the microphone 36 and is sensed by the voice activity detector to freeze the adaptive algorithm being utilized by the adaptive filter 56 so the adaptive algorithm thereafter will not be changed to further affect the speech which is picked up by the first sound sensor 36. In this way the processing which is being performed by the adaptive filter 56 using the adaptive algorithm is frozen so that it does not change as long as voice is being picked up by the sound sensor 36. As soon as there is a pause or there is no voice being picked up by the first sound source 36, the adaptive filter 56 is again permitted to vary the adaptive algorithm to correspond to the environmental noise being received on the second sound sensor 41 to provide an appropriate signal to suppress the environmental noise on the communication link 26. This freezing of the adaptive algorithm in the adaptive filter 56 during the time when speech is taking place does not appreciably affect the noise cancellation characteristics of the present invention because the quietness occurring during speech typically is not of long duration. Thus, in quiet periods during speech by the caller's voice, the adaptive filter 56 is placed in operation, as for example during a few milliseconds or seconds to provide the necessary correction, if any to the adaptive algorithm being utilized by the adaptive filter. Thus it can be seen that appropriate noise suppression can be achieved without affecting the voice of the caller.

The circuitry which is shown in FIG. 3 will not have any affect upon the incoming voice from the recipient and is supplied to the loud speaker 37 in a conventional manner. To overcome ambient environmental noise, it is necessary for the user to press the portion 31a close to the ear to block out surrounding environmental noise and at the same time to cover the other ear with the other hand of the user so that the external environmental noises cannot be heard.

However, if desired, additional means can be provided to provide a zone of quietness around the portion 31a so that the caller can hear even in the presence of environmental noises. Such circuitry is shown in FIG. 4 and as explained previously includes a third sound sensor 46 which is positioned in very close proximity to the speaker 37. The signal from the third sound sensor or error microphone 46 is supplied to another adaptive filter 66 which also receives an input from the second sound source 41. The adaptive filter 66 utilizing this information from the sound sensors 41 and 46 and utilizing an adaptive algorithm in the manner described in co-pending application, Ser. No. 08/206,464, filed Mar. 4, 1994, supplies an output signal to a summer 71. The recipient's voice is received on the link 26 and supplied through an amplifier 72 to the summer 71. The signal which carries the recipient's voice is summed with the external noise signal from the adaptive filter 66 and is supplied through an amplifier 73 to the speaker 37 to provide a sound signal at the output of the speaker 37 which carries the recipient's voice and a signal to suppress the external noise present in the vicinity of the speaker 37 so that there is provided a zone of quietness or noise suppression around the speaker 37 permitting the caller in the noisy environmental location to clearly hear the words being spoken by the recipient. If the noise has not been suppressed to the desired threshold level, this noise above this level is ascertained by the error microphone 46 and an error correction signal is supplied to the adaptive filter 66 so that the adaptive filter 66 through its adaptive algorithm provides a noise suppression signal to the summer 71 that is adequate to suppress the environmental noise at the output of the speaker 37 to a level which is below a desired threshold level.

Thus, with the circuitry shown in FIGS. 3 and 4 it can be seen that the caller in the noisy location, the voice of the caller can be clearly heard by the recipient and similarly the recipient's voice can be clearly heard by the caller even though the caller may be in a very noisy environment. However, for the caller in the noisy environment to clearly hear the recipient's voice free of the external environmental noise it will be necessary for the caller to close off his other ear with his other hand.

In FIG. 5, there is shown a graph in which the ordinate is in volts and the abscissa is in time and in which the external noise shown in a waveform 76 ranging from 0–100 millivolts is attenuated between 30–40 dB within one second. Such attenuation is more than adequate to bring the external noise down to an acceptable threshold level so that the recipient can clearly hear the caller and that the caller can clearly hear the recipient.

In connection with the present invention it can be seen that the noise suppression is being carried out electronically and internally of the system.

From the foregoing it can be seen that there has been provided an active electronic noise suppression system particularly useful for telephone handsets and a method which makes it possible for a caller at a noisy location to be clearly heard by the recipient and similarly for the caller to clearly hear the recipient. Although the present invention has been described principally with a single noisy location, it should be appreciated that the same principles can be utilized when both the caller and recipient are located in noisy locations. It is merely necessary that both locations be provided with the circuitry of the present invention. Also from the foregoing it can be seen that the present invention can be utilized in many different locations where environmental noise is a problem. Thus, in addition to being useful in car phones and air phones, it can be useful in connection with pay telephones at noisy locations.

What is claimed is:

1. A system for use by a caller at one location and a recipient at a remote location of a telephone call from the caller for suppressing actual environmental noise in the vicinity of a telephone being used by the caller comprising a telephone handset forming a part of the telephone being used by the caller, the telephone handset having a first audible sound sensor facing in one direction for picking up human voice sounds emanating from a first direction and creating a first electrical signal and a speaker for producing substantially directional human voice sounds, a second audible sound sensor carried by the telephone handset and facing in direction opposite to said one direction and having sound pick-up capabilities from a direction which is generally opposite said first direction for picking up actual environmental noise in the vicinity of the handset and producing a second electrical signal having a frequency and phase, means including an adaptive filter for processing and performing adaptive filtering of the second electrical signal to provide a third electrical signal of the same frequency as the second electrical signal but 180° out of phase and combining means for combining the third electrical signal with the first electrical signal to provide an output to suppress the actual environmental noise present in the first electrical signal so that the recipient of the telephone call from the caller will receive an electrical signal from the telephone being used by the caller in which the actual environmental noise in the vicinity of the telephone handset of the telephone being used by the caller has been suppressed, said means for processing the second electrical signal including voice activity detector means coupled to the first and second audible sound sensors and to the adaptive filter for sensing when the voice sounds are being picked up by the first audible sound sensor, said voice activity detector means including means for controlling the adaptive filter so that the adaptive filtering does not change when the voice activity detector senses that the voice sounds are being picked up by the first audible sound sensor.

2. A system as in claim 1 together with means for monitoring the output of the combining means to supply an error signal to the adaptive filter when the actual environmental noise has not been suppressed below a threshold level.

3. A system for use by a caller at one location and a recipient at a remote location of a telephone call from the caller for suppressing actual environmental noise in the vicinity of a telephone being used by the caller comprising a telephone handset forming a part of the telephone being used by the caller, the telephone handset having a first audible sound sensor facing in one direction for picking up human voice sounds emanating from a first direction and creating a first electrical signal and a speaker for producing substantially directional human voice sounds, a second audible sound sensor carried by the telephone handset and facing in a direction opposite to said one direction and having sound pick-up capabilities from a direction which is generally opposite said first direction for picking up actual environmental noise in the vicinity of the telephone handset and producing a second electrical signal having a frequency and phase, means for processing the second electrical signal to provide a third electrical signal of the same frequency as the second electrical signal but 180° out of phase, means for combining the third electrical signal with the first electrical signal to provide an output to suppress the actual environmental noise present in the first electrical signal so that the recipient of the telephone call from the caller will receive an electrical signal from the telephone being used by the caller in which the actual environmental noise in the vicinity of the telephone handset being used by the caller has been suppressed, the remote location having a telephone and a handset being used by the recipient for generating an electrical signal representing the recipient's voice, a third audible sound sensor creating a fourth electrical signal mounted on the telephone handset of the caller in the vicinity of the speaker and closer to the speaker than the first and second audible sound sensors and means for processing the second and fourth electrical signals to supply an actual environmental noise cancellation signal, means for combining the noise cancellation signal with the electrical signal representing the recipient's voice and supplying the noise cancellation signal and the electrical signal representing the recipient's voice to the speaker so that a region is created in front of the speaker which is substantially free of the actual environmental noise to permit the caller to hear the recipient's voice substantially free of the actual environmental noise.

4. In a method for suppressing actual environmental noise which is present at the site of a caller in a telephone system in which the caller is making a call to a recipient at a remote location, creating at the site of the caller a first electrical signal having a frequency and phase corresponding to the actual environmental noise at the site of the caller coming from a first direction, processing the first electrical signal to provide a second electrical signal which is of the same frequency but 180° out of phase with the first electrical signal, providing an electrical signal corresponding to the voice of the caller when present coming from a direction opposite of said first direction and combining the first electrical signal of the voice of the caller with the second electrical signal to provide a combined third electrical signal at the remote location in which the caller's voice is present and is free of the actual environmental noise emanating at the site of the caller, checking the combined third electrical signal to ascertain whether any noise is present in the combined third electrical signal and correcting the processing of the first electrical signal so that a combined third electrical signal is provided which is substantially free of noise, ascertaining when the caller is speaking and preventing further correction of the processing of the first electrical signal during the time the caller is speaking.

5. In a method for suppressing actual environmental noise which is present at the site of a caller in a telephone system in which the caller is making a call to a recipient at a remote location, creating at the site of the caller a first electrical signal having a frequency and phase corresponding to the actual environmental noise at the site of the caller coming from a first direction, processing the first electrical signal to provide a second electrical signal which is of the same frequency but 180° out of phase with the first electrical signal, providing an electrical signal corresponding to the voice of the caller when present coming from a direction opposite of said first direction and combining the electrical signal of the voice of the caller with the second electrical signal to provide a combined third electrical signal at the remote location in which the voice of the caller is present and is free of the actual environmental noise emanating at the site of the caller, providing a fourth electrical signal corresponding to the actual environmental noise at the site of the caller, providing an electrical signal corresponding to the voice of the recipient and processing the fourth electrical signal and the electrical signal corresponding to the voice of the recipient to provide a region in the vicinity of the caller in which the actual environmental noise at the site of the caller is suppressed so that the recipient's voice can be heard by the caller free of the actual environmental noise at the site of the caller.

6. A method as in claim 5 further including the step of creating a fifth electrical signal corresponding to the actual environmental noise at the region in the vicinity of the caller and supplying the fifth electrical signal to the region in the vicinity of the caller so that the actual environmental noise in the region in the vicinity of the caller is below a predetermined level.

* * * * *